United States Patent [19]
Sjogren et al.

[11] Patent Number: 5,470,531
[45] Date of Patent: Nov. 28, 1995

[54] EXCHANGER AND METHOD FOR MANUFACTURING THE SAME

[75] Inventors: Axel Sjogren, Littleton; Gary Carson, Golden; Steve Estergreen, Wheat Ridge; Timothy Taga, Broomfield; Rodger Stewart, Lafayette, all of Colo.

[73] Assignee: Cobe Laboratories, Inc., Lakewood, Colo.

[21] Appl. No.: 970,781

[22] Filed: Nov. 3, 1992

[51] Int. Cl.$^6$ .............................. B01D 61/00; A61M 1/14
[52] U.S. Cl. .............................. 422/46; 422/48; 264/339; 156/308.2; 156/308.4; 165/102; 165/165; 493/395; 210/645; 210/321.72; 210/321.77; 210/321.88
[58] Field of Search ........................ 422/46, 48; 264/339; 493/395; 210/645, 321.72, 321.77, 321.86; 165/165, 102; 156/308.2, 308.4

[56] References Cited

U.S. PATENT DOCUMENTS

| | | | |
|---|---|---|---|
| 3,370,710 | 2/1968 | Bluemle, Jr. | 210/321 |
| 3,489,647 | 1/1970 | Kolobow | 196/1.8 |
| 3,788,482 | 1/1974 | Markley | 210/321 |
| 4,028,252 | 6/1977 | Morris | 210/321 |
| 4,163,721 | 8/1979 | Lobdell | 210/321 |
| 4,199,457 | 4/1980 | Esmond . | |
| 4,219,422 | 8/1980 | Knothe et al. | 210/137 |
| 4,228,125 | 10/1980 | Lobdell et al. | 422/46 |
| 4,239,625 | 12/1980 | Hlavinka | 210/321.3 |
| 4,246,121 | 1/1981 | Corbin, III et al. | 210/321.3 |
| 4,267,044 | 5/1981 | Kroplinski et al. | 210/321.2 |
| 4,431,539 | 2/1984 | Borsanyi | 210/232 |
| 4,451,562 | 5/1984 | Elgas et al. | 435/2 |
| 4,455,230 | 6/1984 | Elgas et al. | 210/232 |
| 4,645,645 | 2/1987 | Martinez et al. | 422/46 |
| 4,663,125 | 5/1987 | Gordon et al. | 422/48 |
| 4,863,603 | 9/1989 | Lehmann et al. . | |
| 4,929,354 | 5/1990 | Meyering et al. | 210/321.61 |

FOREIGN PATENT DOCUMENTS

| | | |
|---|---|---|
| 0122022 | 10/1984 | European Pat. Off. . |
| 0285993 | 10/1988 | European Pat. Off. . |
| 2643268 | 8/1990 | France . |
| WO/82/00102 | 1/1982 | WIPO . |

OTHER PUBLICATIONS

Hot Plate Welders, Ultrasonic Welders, Spin Welders, Vibration Welders, Thermo Stakers, Leak Testers; Sales Brochure, Forward Technology Industries Inc., Minneapolis, Minn., Jun. 1991.
Pall Blood Filter Brochure, Pall Corporation, 1984.

*Primary Examiner*—Robert J. Warden
*Assistant Examiner*—N. Bhat
*Attorney, Agent, or Firm*—Finnegan, Henderson, Farabow, Garrett & Dunner

[57] ABSTRACT

An exchanger for oxygenating blood includes a casing having walls and a cavity, sheet material with first and second ends covering distal edges of the walls, and a cover extending over the cavity to sandwich the first and second ends of the sheet material between the cover and the edges of the walls. The cover is melted into the sheet material and the distal edges of the walls. In another embodiment, a blood oxygenator includes a first compartment having a closed casing divided by a folded sheet of membrane material forming a first blood chamber and a first gas chamber. The casing has first and second manifolds in fluid communication with the first blood chamber. A second compartment is interconnected with the first compartment and has a closed casing divided by a folded sheet of membrane material forming a second blood chamber and a second gas chamber. The casing has third and fourth spaced apart manifolds in fluid communication with the second blood chamber. A first conduit connects an outlet of the first manifold to the an inlet of the third manifold, and a second conduit connects an outlet of the fourth manifold to an inlet of the second manifold.

12 Claims, 6 Drawing Sheets

EXCHANGER AND METHOD FOR MANUFACTURING THE SAME

BACKGROUND OF THE INVENTION

1. Field of the Invention

The invention relates to membrane exchangers such as those used for oxygenating blood, and heat exchangers such as those used to adjust the temperature of extracorporeally circulating blood during heart surgery.

2. Description of the Related Art

During open heart surgery, natural cardiovascular activity is suspended, which causes the lungs to collapse. It is, therefore, necessary to simulate the function of the lungs, which replace carbon dioxide in the blood with oxygen. Blood oxygenators serve this function. The typical blood oxygenator includes a membrane that acts as a boundary between extracorporeal blood flow and oxygen flow. As blood and oxygen pass over opposite sides of the membrane, oxygen passes through the membrane and into the blood and carbon dioxide passes, in the opposite direction, through the membrane and into the oxygen stream.

A heat exchanger may have a similar structure except that rather than employing a membrane boundary, the boundary layer is made of a non-permeable heat conducting layer. In use, blood is passed over one side of the boundary layer and a heat exchange fluid is passed over the other. In this manner a heat exchange occurs and the temperature of blood is thereby adjusted at a desired value.

Membrane exchangers and heat exchangers have various biomedical and non-medical uses in addition to blood oxygenating and cooling, and therefore the scope of this application is not limited to oxygenation and blood cooling.

A typical membrane exchanger includes an elongated sheet of membrane material folded into a plurality of pleats and sealed within a casing. Internal compartments are located on opposite sides of the casing for receiving the flap ends of the sheet material. A urethane sealant is introduced into the internal compartments to form a seal between the sheet material and the casing. Similarly, urethane resin seals the sheet material to other internal portions of the casing in order to direct fluid flow and prevent blood leakage across the boundary layer.

There are a number of drawbacks with related art devices. First, while urethane resins are generally recognized as being biocompatible, it is preferable to minimize the number of materials with which extracorporeally circulating blood comes into contact. In addition, when urethane resins are used as seals, the resin may become absorbed to varying degrees across individual folds in the sheet material. This can lead to very slight pockets of stagnated blood and can also cause differences in performance characteristics between similar exchangers.

Another problem with the use of urethane resin is that it requires a curing time of at least one and a half hours before the unit can be tested. Due to the critical nature of the fluid pathway integrity in a blood oxygenator, each unit is typically individually tested at the end of the manufacturing process. From urethane injection and the testing increases considerably the overall manufacturing process time.

Another drawback of related art devices is their size and weight. The use of urethane resin as a sealant adds considerable weight to the exchanger. In fact, the amount of urethane resin that is necessary to seal an exchanger weighs nearly as much as all of the other components of the exchanger combined. In addition, the internal compartments for receiving the ends of the sheet material and allowing a flow path for the urethane add size to the oxygenator. An oxygenator designed with internal compartments for sealing the ends of the sheet material also wastes material because, typically, ⅜ of an inch of material is sealed in resin on each side of the exchanger.

SUMMARY OF THE INVENTION

An object of the invention is to provide an exchanger that minimizes the number of different types of materials with which the fluid flowing through the exchanger must come into contact.

Another object of the invention is to provide an exchanger that can be uniformly manufactured with a minimal amount of performance differences between manufactured units.

A further object of the invention is to provide an exchanger of reduced size and weight.

An additional object of the invention is to provide an exchanger that can be leak tested shortly after manufacture.

A final object of the invention is to provide an exchanger that minimizes the amount of wasted boundary layer material.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purposes of the invention, as embodied and broadly described herein, the invention comprises an exchanger manufacturing method including the steps of folding sheet material into a series of pleats, placing the folded sheet material in a casing having an opening defined by walls with distal edges, covering the distal edges with sheet material, and affixing a cover to the casing by melting a portion of the cover and contacting the cover with the sheet material covering the distal edges of the walls.

It is also preferable to melt a large portion of the cover and to contact the cover with the apices of the pleats of the sheet material so that a shunt block is formed between the cover and the sheet material. The side walls of the casing may be melted in a similar way to seal sides of the casing to the sheet material.

The invention also includes an exchanger with a casing having walls defining a cavity, the walls including distal end edges, a quantity of sheet material having first and second ends covering the distal end edges of the walls, and a cover extending over the cavity the cover being melted to the sheet material and the distal and end edges of the walls.

Both the method and the apparatus of the invention may include a dual compartment oxygenator for selectively permitting an operator to use one or both compartments. A heat exchanger may be integrally connected to the dual compartment oxygenator in accordance with the invention.

It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention, and together with the

DESCRIPTION OF THE PREFERRED EMBODIMENTS

Reference will now be made in detail to the present preferred embodiments of the invention, examples of which are illustrated in the accompanying drawings. Wherever possible, like reference numerals are used to designate the same or like parts.

Figure 1:
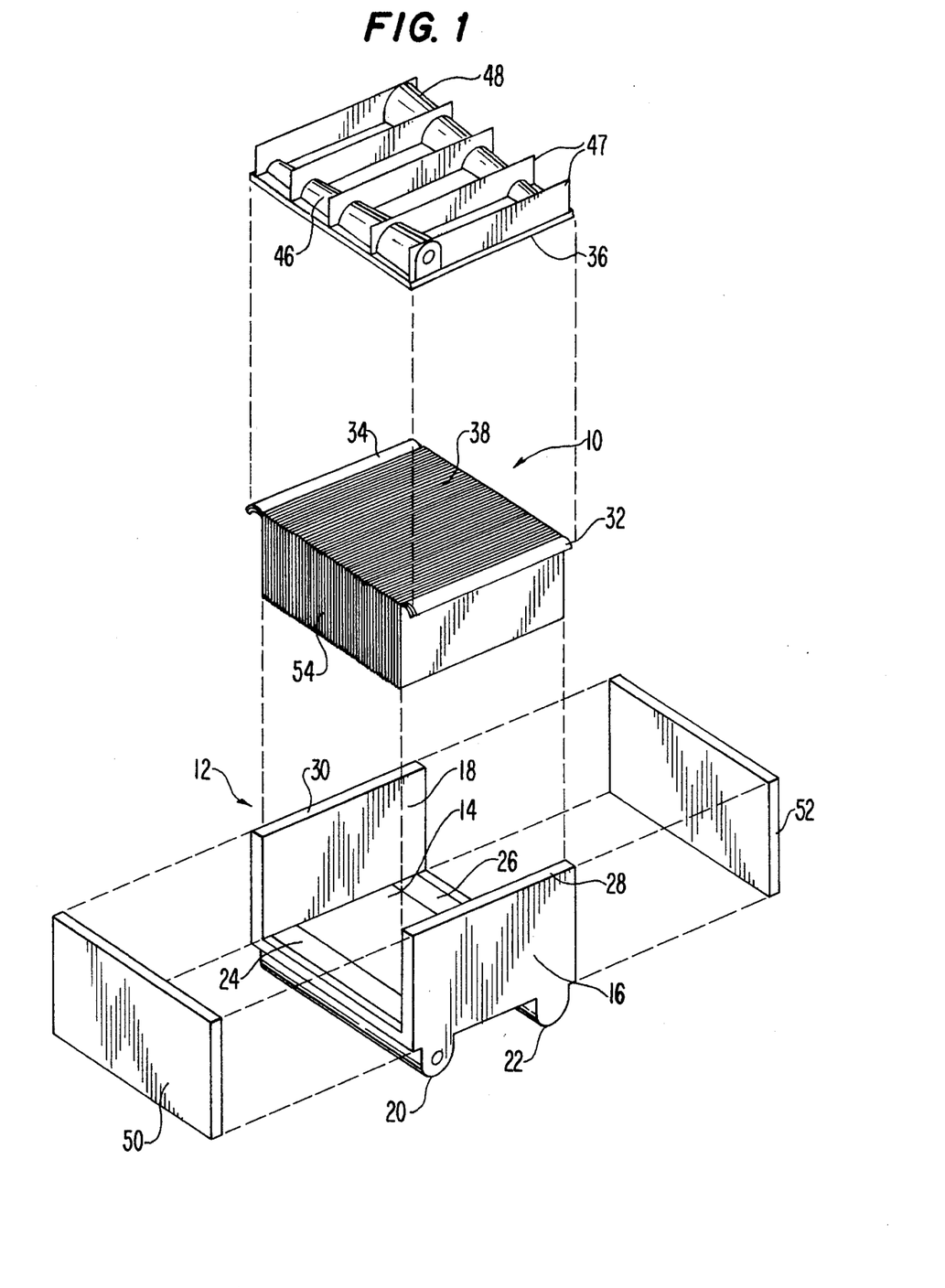
FIG. 1 is an exploded view of a first embodiment of the present invention.

In accordance with the present invention there is provided an exchanger manufacturing method comprising the step of folding sheet material in a series of pleats having apices. As embodied herein, and as illustrated in FIG. 1, the folded sheet material may include membrane 10 which is manufactured from an elongated sheet of membrane material which is folded in a serpentine pattern using a conventional pleating machine. In a preferred embodiment, the membrane is constructed of a membrane material consisting of a layer of polypropylene membrane sandwiched between two layers of polypropylene netting. The height, length, number of folds, netting specification, and membrane specification determine the performance of the exchanger. While various membrane material constructions are possible in accordance with the present invention, it is preferable to use a layer of netting on each side of the membrane in order to act as a spacer for aiding flow between the folds on both sides of the membrane. By way of example only, the membrane may have a thickness of between 1.8 and 2.2 thousandths of an inch, and the netting may have a thickness of between 15 and 25 thousandths of an inch. The netting may be constructed of a series of strands with a pitch of 15 strands per inch in both directions. The membrane material may include a series of pores, each pore having a dimension of $2/10$ of a micron in one direction and 1.2 microns in the other direction. This structure permits gas to pass through the membrane but does not permit liquid to pass through.

If the invention is to be used as a heat exchanger rather than a membrane exchanger, the sheet material may be a non-permeable plastic sheeting.

Also in accordance with the present invention there is provided the step of placing the folded sheet material in a casing having an opening defined by walls with distal edges. As embodied herein, folded sheet material 10 is placed within U-shaped casing 12 which is defined by a bottom wall 14 and two end walls 16 and 18. End walls 16 and 18 include distal edges 28 and 30, respectively. A pair of manifolds 20 and 22 extend along opposite edges of the bottom wall between side walls 16 and 18. Manifolds 20 and 22 include elongated openings 24 and 26, respectively, for channeling fluid to and from membrane 10. An aperture at one end of each manifold 20, 22 forms respectively, a fluid inlet and outlet.

Figure 2:
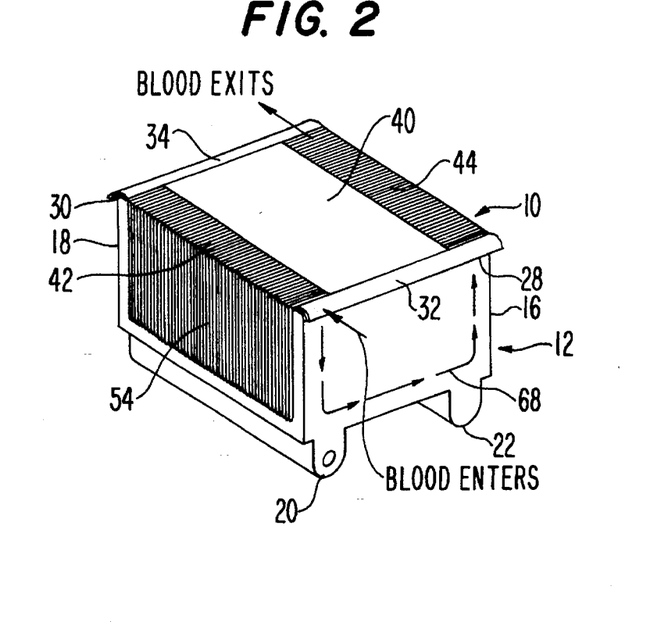
FIG. 2 illustrates the exchanger of FIG. 1 with the sheet material inserted in the casing and the cover, and side walls removed.

In accordance with the present invention there is also provided the step of covering the distal edges with portions of sheet material. As embodied herein and as illustrated in FIG. 1, folded sheet 10 includes end flaps 32 and 34. As illustrated in FIG. 2, when folded sheet 10 is inserted into casing 12, end flaps 32 and 34 respectively cover the edges 28 and 30 of end walls 16 and 18.

In accordance with the present invention, there is provided a step of affixing a cover to the casing by melting a portion of the cover and contacting the cover with the sheet material covering distal edges of the walls. As illustrated in FIG. 1, cover 36 includes a pair of manifolds 46 and 48, similar in structure to manifolds 20 and 22. A series of ribs 47 may be provided on cover 36 to add structural support to cover 36.

The preferred method for affixing cover 36 to casing 12 is by first contacting internal surface portions of cover 36 with a heated platen. Cover 36 is preferably manufactured of a meltable material such as polypropylene, and it is preferable to melt between 0.01 and 0.02 inches of the interior surface of cover 36 with the heated platen. At the same time that the cover is melted, the flaps 32 and 34 and the distal edges 28 and 30 of the end walls 16 and 18 are also melted. Once sufficient melting has occurred, cover 36 is pressed against the distal edges 28 and 30 of end walls 16 and 18. In this manner, the end flaps of membrane material 32 and 34 are sandwiched between cover 36 and end walls 16 and 18, respectively. As the melted portion of the cover cools and solidifies, the cover, the flaps 32 and 34, and the end wall integrally bond, thereby forming a leak-proof seal between the end walls and sheet 10, and fixing the ends of sheet 10 in place.

Figure 3:
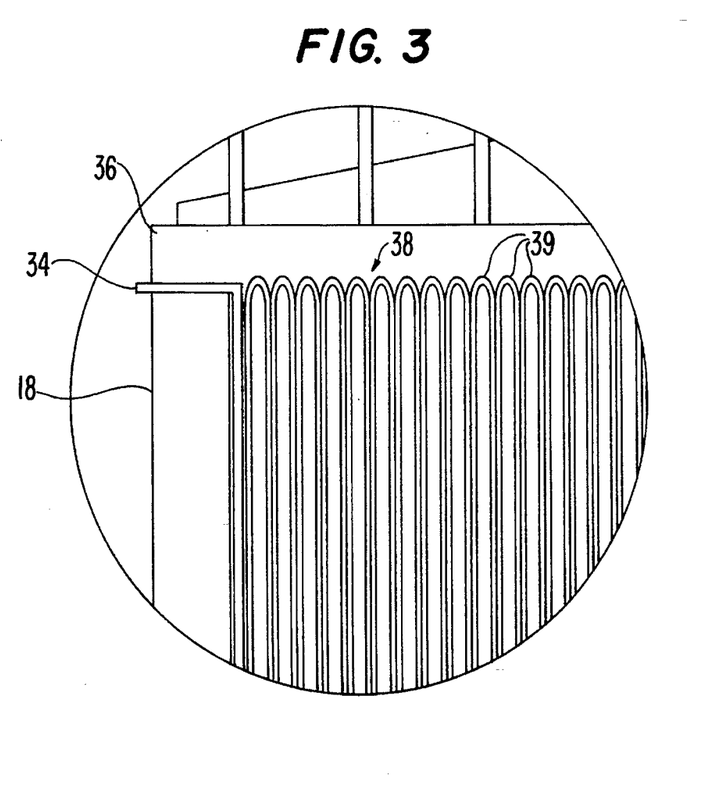
FIG. 3 is an enlarged detail view of the interconnection of the sheet material, the cover and an end wall of the exchanger illustrated in FIG. 1.

Likewise, if a central portion of cover 36 is also melted with the heated platen, as cover 36 is pushed against pleated surface 38 of folded sheet 10, the apices 39 of the pleats become embedded in the internal surface of melted cover 36, as illustrated in FIG. 3. As the cover cools and solidifies, the apices of the pleats integrally bond with the cover forming a shunt block. As illustrated in FIG. 2, the area 40 of the shunt block is located at a central portion of pleated surface 38. However pleated surface 38 is not bonded to cover 36 in manifold areas 42 and 44, so that fluid may enter and exit the folds of sheet 10 in these areas.

Depending upon desired use, it may be preferable to provide a shunt block on both sides of folded sheet 10. If desired, a similar bonding process can be used to bond an opposite pleated surface of folded sheet 10 to the bottom 14 of casing 12. It is preferable to provide this dual shunt block using hot plate welding process. However, one of the seals may be formed by hot plate welding and the other may be formed using a wide strip of pressure sensitive adhesive tape between the pleated surface of the membrane and the bottom of the encasing.

Side walls 50 and 52 complete the encapsulation of the folded sheet 10, and are sealed to the encasing using a heated platen in a manner similar to the manner in which cover 36 is sealed to the encasing 12. When sealing side walls 50 and 52, it is preferable to not only heat the internal surfaces of the side walls with a heated platen, but also to separately heat the side surfaces 54 of folded sheet 10. During this heating procedure, it is preferable to melt between 0.1 and 0.2 inches of side surfaces 54. By melting at least 0.05 inches of side surfaces 54, it can be ensured that no leakage will occur between opposite sides of the folded sheet material at the interconnection with side walls 50 and 52.

The invention permits a folded sheet to be sealed within an encasing without the use of urethane resins which add significant weight, additional opportunity for contamination, and nonuniformity in performance. Moreover, a particular advantage of using heat welding for assembling the various elements of the membrane exchanger is to provide the casing with a very good mechanical resistance, the casing forming an integral unit. However, it should be noted that the invention, in its broadest sense, is not limited to an exchanger that is completely resin free. For example, it may be desirable to use resin for certain functions and heated platen welding for other functions.

Operation of the invention will now be described in connection with FIG. 2, which illustrates an exchanger having its cover and side walls removed. For the purposes of this example, the exchanger will be described in connection with oxygenation of blood. However, as discussed earlier, the invention is not limited to this use.

During cardiovascular surgery, when the lungs are collapsed, blood is withdrawn from the patient and enters the exchanger through manifold 46 in cover 36 (illustrated in FIG. 1). The blood flows along inlet surface 42 of pleated surface 38. Shunt block 40 prevents blood from shunting across surface 38; therefore the blood has no alternative but to move into the folds of the pleated membrane 10. Blood then flows through the pleats of the membrane in a pattern as illustrated by arrows 68 in FIG. 2, and exits from manifold 48 located on an opposite side of shunt block 40 from manifold 46.

Simultaneously, oxygen is supplied to the opposite side of the encasing through manifold 20 and moves on an opposite side of the membrane between the folds of the membrane in a pattern similar to the blood flow pattern illustrated by arrow 68. As the oxygen passes between the folds of the membrane, it passes through the membrane and into the blood, thereby oxygenating the blood. At the same time, carbon dioxide passes through the membrane, in the opposite direction, and into the oxygen stream. Excess oxygen exits the exchanger through manifold 22.

When used as a blood oxygenator, the membrane exchanger described in connection with FIGS. 1 and 2 is capable of processing up to 4.5 liters of blood per minute with an oxygen transfer rate of up to 38/ml/min/LPM blood flow at a barometric pressure of approximately 620 mmHg. These flow and transfer rates can be achieved while maintaining AAMI (Association for the Advancement of Medical Instrumentation) standard inlet and outlet conditions, (i.e., 150 torr outlet pressure).

Figure 4:
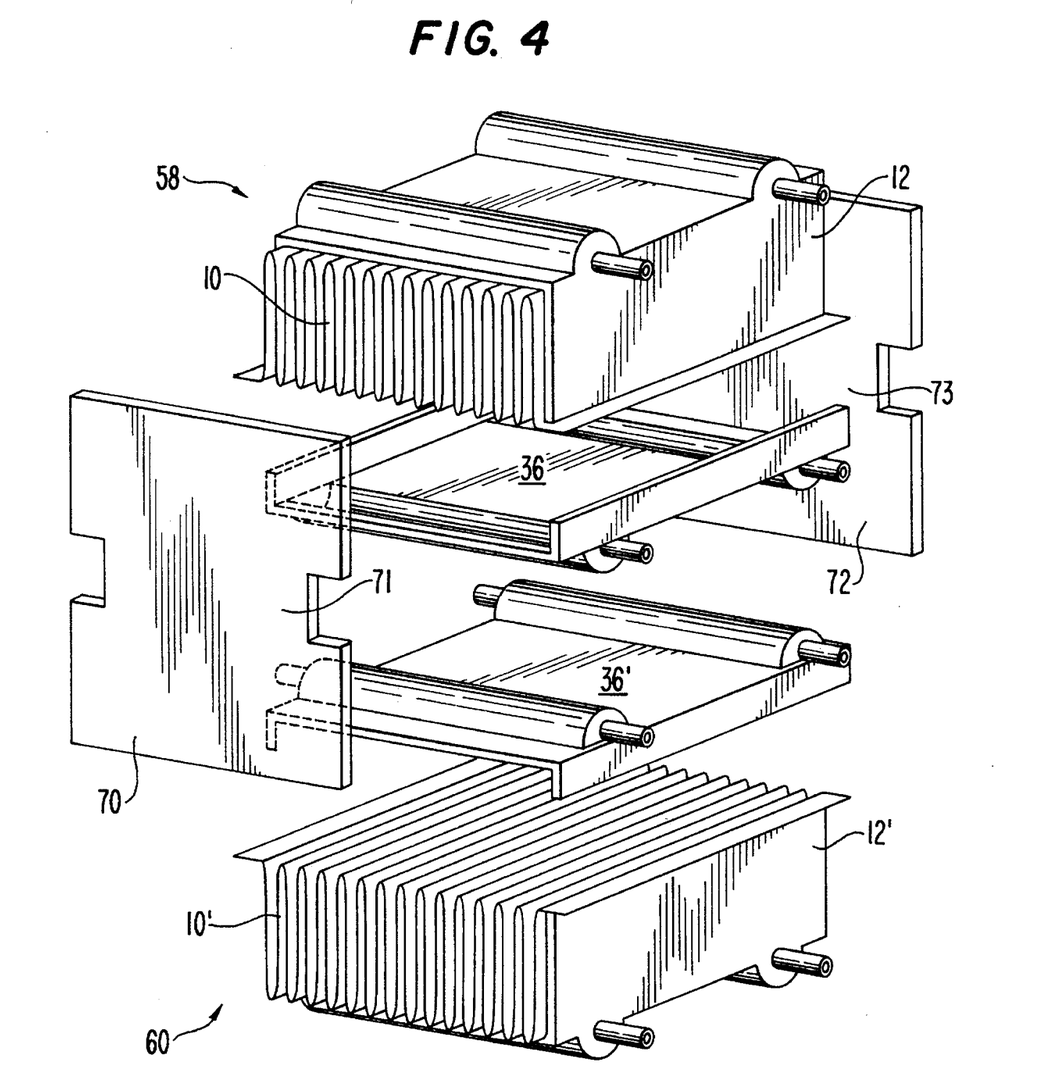
FIG. 4 is an exploded view of a second embodiment of the present invention.

As illustrated in FIG. 4, a membrane exchanger of the present invention can be manufactured as a dual unit having sides 56 sufficient in size to cover two separate exchangers 58 and 60. There are a number of reasons why a dual unit exchanger may be preferable to a single compartment exchanger of the same capacity. First, it may be easier to manufacture a double compartment exchanger than one large exchanger with a membrane having the same surface area. In addition, a double compartment exchanger may be more compact than one large compartment exchanger of the same capacity. Finally, from a therapeutic point of view, the dual compartment permits a physician to increase the oxygenation rate during a treatment session if the patient requires more oxygenation than originally foreseen.

Each of exchangers 58 and 60 are substantially identical to the exchanger illustrated in FIG. 1. The dual unit includes a pair of folded sheets 10,10'; a casing made up of two subcasings 12,12', and a pair of covers 36,36'. The exchangers 58 and 60 are held together by a pair of side walls 70 and 72 that serve as side walls for both of the exchangers 58 and 60. Each of walls 70 and 72 have an intermediate portion 71 and 73, respectively, that extends between and connects exchanger subunits 58 and 60. Thus, when manufacturing this dual unit, each of the subunits is manufactured simultaneously, with the final production step including attaching the side walls 70 and 72 to the subunits to simultaneously complete the encapsulation of both subunits. This final step is preferably accomplished using the heat welding technique described in connection with FIG. 1, except that with the dual unit, the edges of both subunits must be simultaneously heated along with a respective side wall, and then the respective side wall is mated with both subunits at the same time, and permitted to cool to thereby form a leak-proof bond with both subunits.

Figure 5:
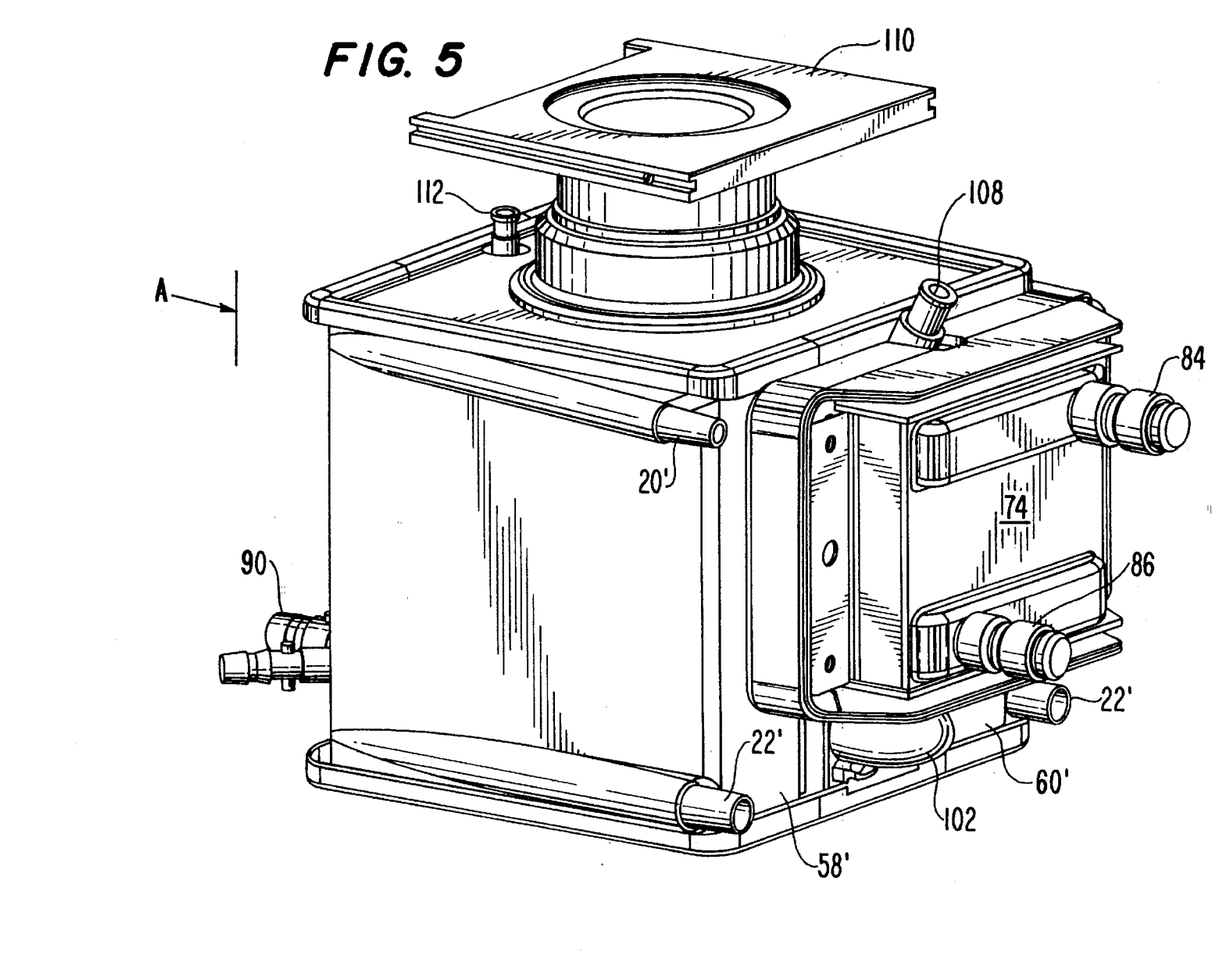
FIG. 5 is a perspective view of a third embodiment of the present invention.
Figure 6:
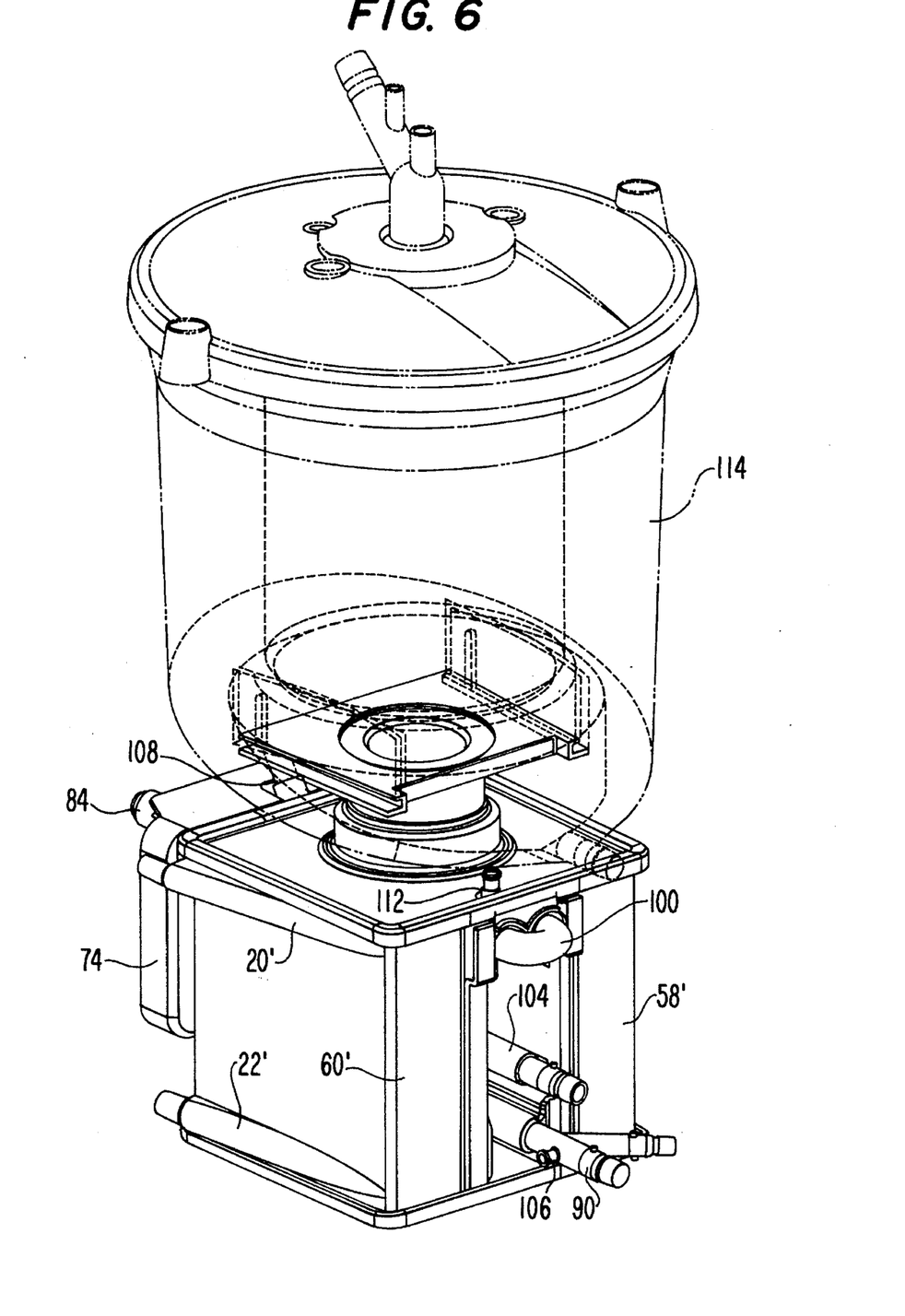
FIG. 6 is a perspective view of the third embodiment of the invention as viewed from the direction A in FIG. 5 and illustrating the placement of a cardiotomy reservoir thereon.
Figure 7:
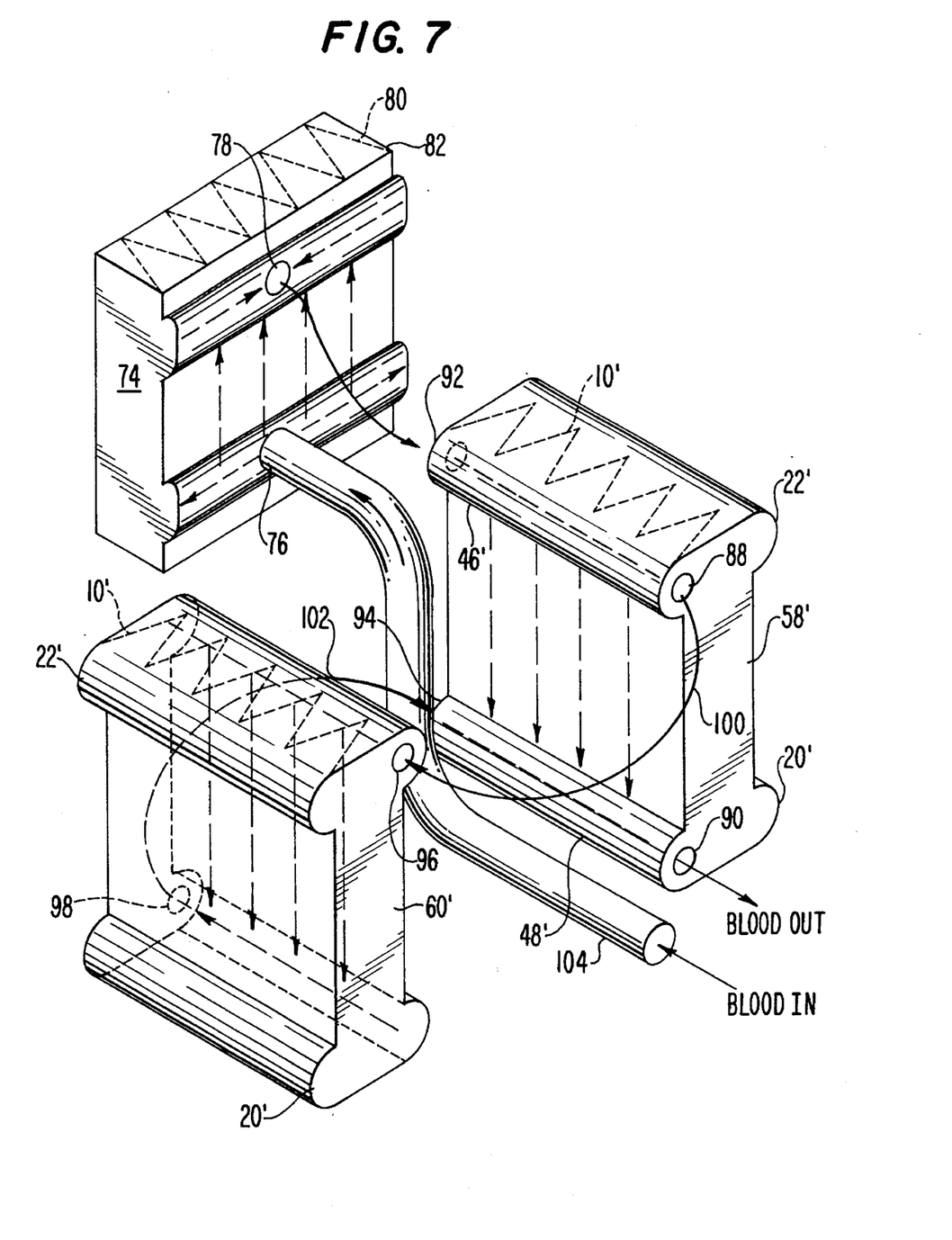
FIG. 7 is a diagram schematically illustrating liquid flow through the apparatus of FIG. 6.

A third embodiment of the invention illustrated in FIGS. 5–7 is similar to the embodiment of FIG. 4, with the addition of structure including a heat exchanger. The third embodiment of the invention includes a pair of oxygenators 58' and 60' connected to heat exchanger 74, and the oxygenators may be assembled in the manner described in connection with FIG. 4. Heat exchanger 74 includes a blood inlet 76 and a blood outlet 78, as schematically illustrated in FIG. 7. The blood inlet and outlets permit blood to flow on one side of folded exchanger sheet 80 located within casing 82. Similarly, heat exchanger 74 includes a heat exchange fluid inlet 84 and outlet 86 (illustrated in FIG. 5) for permitting heat exchange fluid to circulate on a side of folded exchanger sheet 80 opposite to the side on which blood flows.

Exchanger sheet 80 is made of a non-permeable material such as stainless steel foil or thin plastic, and in the latter case, may be constructed in a manner described in connection with FIG. 1. Alternatively, the entire heat exchanger 74 including casing 82 may be constructed of stainless steel. A temperature probe 108 extends into the inlet manifold 46' of oxygenator 58' to permit measurement of blood temperature.

Oxygenator 58' includes a pair of blood outlet ports 88 and 90, and a pair of blood inlet ports 92 and 94. The blood outlet port 78 of heat exchanger 74 is connected to blood inlet port 92 on manifold 46' of oxygenator 58', and the outlet port 90 of manifold 48' is for connection to a cannula for return of oxygenated blood at a desired temperature to a patient under treatment. Blood outlet 90 may include a sample port 106 for permitting access to the treated blood before return to the patient.

The remaining blood outlet port 88 and blood inlet port 94 permit oxygenator 58' to be connected to oxygenator 60' for use when a single oxygenator is insufficient for a specific treatment.

Oxygenator 60' includes a single blood inlet 96 and a single blood outlet 98, which are respectively connected to blood outlet 88 and blood inlet 94 of oxygenator 58' through lines 100 and 102, respectively. A degassing port 112 is provided proximate to blood inlet 96 for permitting excess gas to escape from the blood side of the circuit. In operation, degassing port 112 is connected to 10 a cardiotomy reservoir 114 by tubing fitted with a valve, which allows for degassing of the blood chamber without the need for recirculation. If, during a treatment session the second compartment 60' is needed and if no degassing port 112 were to be provided, a recirculation procedure would be necessary in order to degas the second compartment 60'. A rotatable support 110 is mounted atop the integrated unit for supporting the cardiotomy reservoir 114, allowing for the shortest possible connection between the reservoir and a blood circulation pump. This structure is preferred because it is always desirable, in an extracorporeal blood circuit, to limit the amount of blood circulating outside of the body.

When heat exchanger 74 and oxygenators 58' and 60' are interconnected as illustrated in FIG. 6, a void is formed between oxygenators 58' and 60' through which a blood inlet line 104 passes. Blood inlet line 104 is connected to blood inlet port 76 of heat exchanger 74. Finally, each of oxygenators 58' and 60' are provided with oxygen inlet and outlet manifolds 20' and 22', respectively, for circulating oxygen on a side of membrane 10' opposite the side on which blood flows.

Operation of the third embodiment of the invention will now be described in connection with FIG. 7. During cardiac surgery when the human lungs are dysfunctional, blood is withdrawn from a patient and is supplied to blood inlet line 104 via a pump (not shown). The blood enters heat exchanger 74 through blood inlet port 76 where it flows between the pleats on one side of heat exchange sheet 80. Simultaneously, heat exchange fluid is circulated through the pleats on an opposite side of sheet 80, the heat exchange fluid being circulated through inlet and outlet ports, 84 and 86, respectively (illustrated in FIG. 5). Heat transfer occurs across sheet 80, thereby allowing the temperature of blood to be adjusted to a desired value.

The blood exits heat exchanger 74 through blood outlet 78 and enters manifold 46' of oxygenator 58' through blood inlet 92. If only one oxygenator is needed for a particular procedure, lines 100 and 102 are obturated using clamps (not shown) and blood flows in-between the pleats on one side of folded membrane 10' of oxygenator 58'. Simultaneously, oxygen enters oxygenator 58' through manifold 20', flows between pleats of membrane 10' on a side of membrane 10' opposite the side on which blood flows, and exits oxygenator 58' through manifold 22'. During this simultaneous flow, oxygen passes through membrane 10' and enters the blood for reinfusion into the patient after the blood leaves oxygenator 58' through blood outlet port 90. At the same time, carbon dioxide from blood passes through the membrane in an opposite direction, and flows away in the oxygen stream.

If two oxygenator units are required during a procedure, lines 100 and 102 are opened permitting a portion of the blood entering inlet port 92 of oxygenator 58' to bypass oxygenator 58' and enter oxygenator 60'. Oxygenator 60' functions in a substantially identical manner to oxygenator 58' except that the single blood outlet 98 of oxygenator 60' is connected to the second blood inlet 94 of oxygenator 58' for reinfusion into a patient through blood outlet 90.

Other embodiments of the invention will be apparent to those skilled in the art from consideration of the specification and practice of the invention disclosed herein. In the above described membrane exchanger, the casing and the membrane material have been described as being made of the same material, namely, polypropylene. It should be noted that different materials could be used, provided that such materials are bondable by heat welding. It is intended that the specification and examples be considered as exemplary only, with a true scope and spirit of the invention being indicated by the following claims.

What is claimed is:

1. An exchanger, comprising:
   a casing having walls defining a cavity, the walls including distal edges;
   a quantity of sheet material having first and second ends covering the distal edges of the walls; and
   a cover extending over the cavity and sandwiching the first and second ends of the sheet material between the cover and the edges of the walls, the cover being melted into the sheet material and the distal edges of the walls.

2. An exchanger as set forth in claim 1 wherein the quantity of sheet material is folded and includes a plurality of pleats having apices.

3. An exchanger as set forth in claim 1 wherein the sheet material includes a membrane sheet sandwiched between two layers of netting material.

4. An exchanger as set forth in claim 3 wherein the quantity of sheet material is folded and includes a plurality of pleats having apices, the apices of the pleats defining first and second pleated surfaces, and wherein at least one of the casing and the cover is melted to one of the first and second pleated surfaces to form a seal therebetween.

5. An exchanger as set forth in claim 1 wherein at least one of the cover and the casing is melted to apices of pleats of the sheet material.

6. An exchanger as set forth in claim 1 wherein the casing defines two cavities and the sheet material includes two separate and folded sheets of membrane material, each folded sheet being located in one of the two cavities and each folded sheet having a plurality of apices and ends for covering distal edges of the casing, the exchanger further including at least one cover for covering the cavities, a portion of said at least one cover being melted to a portion of each of the folded membrane sheets.

7. An exchanger as set forth in claim 4 wherein said at least one cover includes two covers, each for covering one of the cavities and each having a portion that is melted to one of the folded membrane sheets.

8. An exchanger as set forth in claim 6 further including a heat exchanger integrally connected to the casing.

9. An exchanger as set forth in claim 8 wherein the heat exchanger includes a receptacle and a folded sheet of material located in the receptacle.

10. An exchanger as set forth in claim 9 wherein the folded sheet includes a metal layer.

11. An exchanger as set forth in claim 9 wherein the folded sheet includes a plastic layer.

12. An exchanger comprising:
    a quantity of sheet material folded into a plurality of pleats;
    a U-shaped casing, defining a cavity and having a bottom wall connected to two end walls, each of the end walls having a distal edge covered by portions of the sheet material, pleats of the folded sheet material being melted to the bottom wall and having portions covering the distal edges of the walls;
    a cover extending over the cavity and being melted to pleats of the folded sheet material; and
    a pair of side walls extending between the end walls and melted to the sheet material.

\* \* \* \* \*

UNITED STATES PATENT AND TRADEMARK OFFICE
CERTIFICATE OF CORRECTION

PATENT NO. : 5,470,531
DATED : November 28, 1995
INVENTOR(S) : Axel SJOGREN et al.

It is certified that error appears in the above-indentified patent and that said Letters Patent is hereby corrected as shown below:

Claim 7, column 8, line 37, change "claim 4" to --claim 6--.

Signed and Sealed this

Twelfth Day of March, 1996

Attest:

BRUCE LEHMAN

Attesting Officer     Commissioner of Patents and Trademarks